United States Patent
Hammad et al.

(10) Patent No.: US 9,238,598 B2
(45) Date of Patent: Jan. 19, 2016

(54) CARBON DIOXIDE CONVERSION TO HYDROCARBON FUEL VIA SYNGAS PRODUCTION CELL HARNESSED FROM SOLAR RADIATION

(71) Applicant: Saudi Arabian Oil Company, Dhahran (SA)

(72) Inventors: Ahmad D. Hammad, Dhahran (SA); Zaki Yusuf, Dhahran (SA); Stamatios Souentie, Dhahran (SA); Nayif A. Al-Rasheedi, Dhahran (SA); Bandar A. Fadhel, Dhahran (SA); Atef Saeed Al-Zahrani, Dhahran (SA)

(73) Assignee: SAUDI ARABIAN OIL COMPANY (SA)

( * ) Notice: Subject to any disclaimer, the term of this patent is extended or adjusted under 35 U.S.C. 154(b) by 62 days.

(21) Appl. No.: 14/147,067

(22) Filed: Jan. 3, 2014

(65) Prior Publication Data

US 2014/0194539 A1  Jul. 10, 2014

Related U.S. Application Data

(60) Provisional application No. 61/749,063, filed on Jan. 4, 2013.

(51) Int. Cl.
*C07C 1/04* (2006.01)
*C01B 3/38* (2006.01)
(Continued)

(52) U.S. Cl.
CPC .............. *C07C 1/0455* (2013.01); *C01B 3/38* (2013.01); *C10G 2/32* (2013.01); *F03G 6/067* (2013.01);
(Continued)

(58) Field of Classification Search
CPC .............. C01B 2203/0233; C01B 2203/0238; C01B 2203/06; C01B 2203/061; C01B 2203/062; C01B 2203/067; C01B 2203/1241; C01B 3/38; C07C 1/0455; C10G 2/32; F03G 6/067; Y02E 10/46
USPC ...................... 422/186.04; 518/704
See application file for complete search history.

(56) References Cited

U.S. PATENT DOCUMENTS 4,776,171 A   10/1988   Perry, Jr. et al.
5,128,003 A   7/1992   Murdoch et al.
(Continued)

FOREIGN PATENT DOCUMENTS

WO   00/28610 A1   5/2000
WO   2011020825 A1   2/2011

OTHER PUBLICATIONS

Doty, F. D., et al.; Securing our Transportation Future by Using Off-Peak Wind Energy to Recycle CO2 Into Fuel; ASME (American Society of Mechanical Engineers); Jul. 19-23, 2009.
(Continued)

*Primary Examiner* — Jafar Parsa
*Assistant Examiner* — Amy C Bonaparte
(74) *Attorney, Agent, or Firm* — Bracewell & Giuliani LLP; Constance Gall Rhebergen

(57) ABSTRACT

A process for converting carbon dioxide to hydrocarbon fuels using solar energy harnessed with a solar thermal power system to create thermal energy and electricity, using the thermal energy to heat a fuel feed stream, the heated fuel feed stream comprising carbon dioxide and water, the carbon dioxide captured from a flue gas stream, converting the carbon dioxide and water in a syngas production cell, the syngas production cell comprising a solid oxide electrolyte, to create carbon monoxide and hydrogen, and converting the carbon monoxide and hydrogen to hydrocarbon fuels in a catalytic reactor. In at least one embodiment, the syngas production cell is a solid oxide fuel cell. In at least one embodiment, the syngas production cell is a solid oxide electrolyzer cell.

6 Claims, 5 Drawing Sheets

(51) Int. Cl.
*C10G 2/00* (2006.01)
*F03G 6/06* (2006.01)

(52) U.S. Cl.
CPC . *C01B 2203/0233* (2013.01); *C01B 2203/0238* (2013.01); *C01B 2203/06* (2013.01); *C01B 2203/061* (2013.01); *C01B 2203/062* (2013.01); *C01B 2203/067* (2013.01); *C01B 2203/1241* (2013.01); *Y02E 10/46* (2013.01)

(56) References Cited

U.S. PATENT DOCUMENTS

| | | |
|---|---|---|
| 6,769,244 B2 | 8/2004 | Headley et al. |
| 7,132,183 B2 | 11/2006 | Galloway |
| 7,642,292 B2 | 1/2010 | Severinsky |
| 7,704,369 B2 | 4/2010 | Olah et al. |
| 7,752,845 B2 | 7/2010 | Johnson |
| 7,842,264 B2 | 11/2010 | Cooper et al. |
| 7,863,340 B2 | 1/2011 | Severinsky |
| 8,063,305 B2 | 11/2011 | Qin et al. |
| 8,084,652 B2 | 12/2011 | Littleford |
| 8,114,916 B2 | 2/2012 | Severinsky |
| 8,138,380 B2 | 3/2012 | Olah |
| 8,168,143 B2 | 5/2012 | Severinsky |
| 8,277,631 B2 | 10/2012 | Eastman et al. |
| 8,288,446 B2 | 10/2012 | Mamedov et al. |
| 8,366,902 B2 | 2/2013 | Hawkes et al. |
| 2005/0279095 A1* | 12/2005 | Goldman ............... 60/641.8 |
| 2008/0023338 A1* | 1/2008 | Stoots et al. ............ 205/637 |
| 2008/0107932 A1* | 5/2008 | Pham ....................... 429/14 |
| 2009/0235587 A1* | 9/2009 | Hawkes et al. ........... 48/202 |
| 2010/0000874 A1 | 1/2010 | Hinman et al. |
| 2010/0022669 A1 | 1/2010 | Cohn et al. |
| 2010/0137457 A1 | 6/2010 | Kaplan |
| 2010/0237291 A1 | 9/2010 | Simmons et al. |
| 2010/0300892 A1 | 12/2010 | Matare et al. |
| 2010/0305221 A1 | 12/2010 | Schunk et al. |
| 2011/0039956 A1 | 2/2011 | Raisz et al. |
| 2011/0070510 A1 | 3/2011 | McAlister |
| 2011/0250100 A1 | 10/2011 | Juranitch |
| 2012/0010305 A1 | 1/2012 | Grauer et al. |
| 2012/0022172 A1 | 1/2012 | Grauer |
| 2012/0228150 A1 | 9/2012 | Kang et al. |
| 2012/0275987 A1 | 11/2012 | Hiza et al. |
| 2013/0005839 A1 | 1/2013 | O'Connor |

OTHER PUBLICATIONS

Doty, PhD, F. D., et al.; Toward Efficient Reduction of CO2 to CO for Renewable Fuels; ASME (American Society of Mechanical Engineers); May 17-22, 2010.

Kaneco, S., et al.; Electrochemical Reduction of Carbon Dioxide to Hydrocarbons with High Faradaic Efficiency in LiOH/Methanol; The Journal of Physical Chemistry B; 1999; pp. 7456-7460; vol. 103; American Chemical Society.

Roy, S. C., et al.; Toward Solar Fuels: Photocatalytic Conversion of Carbon Dioxide to Hydrocarbons; ACS NANO; 2010; pp. 1259-1278; vol. 4 No. 3; www.acsnano.org; American Chemical Society.

PCT International Search Report and the written opinion dated Apr. 28, 2014; International Application No. PCT/US2014/010152; International Filing Date Jan. 3, 2014.

* cited by examiner

CARBON DIOXIDE CONVERSION TO HYDROCARBON FUEL VIA SYNGAS PRODUCTION CELL HARNESSED FROM SOLAR RADIATION

FIELD OF THE INVENTION

This invention relates to a process and system for the capture of waste gas and the conversion of the waste gas to hydrocarbon fuel. More specifically, this invention relates to a process and system for capturing carbon dioxide ($CO_2$) and water vapor ($H_2O$) and subsequently converting the $CO_2$ and $H_2O$ to hydrocarbon fuel harnessing solar energy.

BACKGROUND OF THE INVENTION

The use of fossil fuels for power generation grows increasingly problematic. First, petroleum consumption has increased even as world-wide petroleum reserves have declined. For example, Saudi Arabia's domestic petroleum consumption due to power generation is expected to be 8 million barrels/day by 2028, which means a reduction of the quantities available for export. Second, concerns about air quality may result in stringent regulations such as a carbon tax aimed at reducing carbon emissions.

Given Saudi Arabia's abundant quantities of solar radiation energy, solar power capture coupled with solar storage represents an opportunity to address both issues. Conventional solar storage and capture systems include photovoltaics and solar thermal systems.

Photovoltaics convert solar energy into electrical current due to the photovoltaic effect of certain substances, such as silicon or organic solar materials. Photovoltaics are capital intensive, but excellent for small scale electricity generation, for example, homes, outdoor lights, highway signs. For larger systems, such as those that contribute to the electricity grid, solar thermal systems, or concentrating solar power (CSP) systems, are preferred. Existing CSP systems include, for example, the linear Fresnel reflector system, the trough system, the dish system, and the tower system.

CSP systems convert solar radiation energy into thermal energy using heliostats. Heliostats are mirrors, typically flat, which are mounted such that they move on an axis to track the movement of the sun during daylight hours. Heliostats concentrate the solar radiation (sunlight) onto a receiver, which uses the thermal energy from the solar radiation to heat a working fluid. The working fluid, a heat transfer fluid, such as water ($H_2O$) or molten salt, exits the heliostat/receiver system where it exchanges heat with $H_2O$ to generate steam. When $H_2O$ is the working fluid, the steam is generated directly from the heated working fluid. The steam runs a steam turbine, which drives a generator to produce electricity.

All CSPs operate under the same basic principles, the differences lie in the shape and layout of the heliostats and the spatial relationship of the heliostats to the receiver. For example, in a linear Fresnel reflector system, the heliostats are long flat tracks of mirrors. The receiver is a tube fixed in space above the mirrors. A trough system uses parabolic mirrors and a tube positioned along the focal line of the reflectors, requiring a large number of reflectors. Dish system CSPs also use parabolic shaped reflectors; a large parabolic dish covered in mirrors directs sunlight to a receiver mounted on the dish along the focal line of the mirrors. A dish system CSP produces relatively little electricity compared to other CSP systems. Tower system CSPs employ large numbers of heliostats typically arrayed in lines. The receiver sits on the top of a tall tower and the heliostats focus the solar energy onto the receiver. A tower CSP is capable of producing up to 200 megawatts of electricity.

In addition to the ability to generate large amounts of electricity, another advantage of solar thermal systems over photovoltaics is the ability to store thermal energy in the working fluid. The working fluids may be stored in tanks until the thermal energy is needed for electricity generation. Thus, allowing generation even when there is no direct sunlight, such as at night or in stormy weather. Even still, the storage of a working fluid is not a long term solution, due to the size of the tanks needed for storage and eventual heat loss. Thus, the conversion of solar thermal energy to fuel is an attractive alternative.

The emission of $CO_2$ into the atmosphere is increasingly under attack. Carbon capture technologies are being explored as a way to remove and store the $CO_2$ from waste gas. Carbon capture technologies are broadly categorized as to whether the capture technology is post-combustion, pre-combustion, or oxyfuel combustion. Post-combustion technologies typically include solvent capture systems, which use a solvent to absorb $CO_2$ from a waste gas stream and then use heat to remove the absorbed $CO_2$ from the solvent stream. The resulting stream is a nearly pure stream of $CO_2$. Post-combustion technologies are commonly used with fossil fuel burning power plants. Other post-combustions technologies include, for example, calcium looping cycle or chemical looping combustion.

Current storage (or sequestration) schemes most commonly include geological sequestration, in which the carbon is stored in underground formations. Depleted oilfields, unmineable coal deposits, and saline formations provide naturally occurring formations appropriate for the storage of $CO_2$. These formations, however, suffer from setbacks including, for example, their locations, the costs to inject the $CO_2$ into the ground, and the concerns about leakage out of the formation at some later point.

An alternative to sequestration of $CO_2$ is to convert the $CO_2$ to other useful components. One way to achieve conversion is using a fuel cell to convert the $CO_2$ with the added benefit of generating electricity. Fuel cells contain three sections: an anode, a cathode, and an electrolyte. Redox reactions occur at the anode and the cathode. In many cases, the overall effect is to convert $H_2O$ to hydrogen ($H_2$) and oxygen ($O_2$).

Fuel cells are categorized by their electrolyte. One category of fuel cells uses a solid oxide electrolyte. Solid oxide fuel cells reduce oxygen on the cathode side, a current is applied to the cathode so that it is negatively charged and conductive. The oxygen ions diffuse through the cathode, the solid oxide electrolyte, and the anode so that oxidation reactions occur on the anode side. The oxidation reactions generate electrons which can be carried through the anode to generate an electricity supply. The anode, cathode, and solid oxide electrolyte of solid oxide fuel cells are composed of ceramic materials and operated at temperatures above 500° C. to ensure the proper functioning of the ceramic materials. The ceramic materials can be porous. Porosity is not required for the passage of oxygen ions from the electrode to the electrolyte. The porosity of the anode impacts the electrolyte/electrode/gas interface area (three phase boundaries), and thus impacts oxygen ion formation rate. The porosity also enhances the diffusivity of molecular oxygen from the gas phase to the three phase boundaries. Solid oxide fuel cells have been shown to have high efficiencies.

A solid oxide fuel cell run in a "regenerative" mode is often called a solid oxide electrolysis cells. Solid oxide electrolysis cells electrolyze components by a reduction process on the cathode side, thus capturing oxygen ions, which diffuse through the cathode, the solid oxide electrolyte, and the anode to form oxygen molecules on the anode side of the cell. The electrolysis of $H_2O$ is endothermic, thus the high operating temperatures of a solid oxide electrolysis cell make the electrolysis reaction thermodynamically favored. In addition, the high temperature increases the kinetics of the reaction. High temperature electrolysis has the advantage of high conversion efficiency, above 90% conversion of $CO_2$ is expected according to some estimates.

SUMMARY OF THE INVENTION

The present invention relates to a process and system for the capture of waste gas and the conversion of the waste gas to hydrocarbon fuel. More specifically, this invention relates to a process and system for capturing carbon dioxide ($CO_2$) and water vapor ($H_2O$) and subsequently converting the $CO_2$ and $H_2O$ to hydrocarbon fuel harnessing solar energy.

In one aspect of the present invention, a process for converting carbon dioxide to hydrocarbon fuels using solar energy is provided. The process includes the steps of receiving direct sunlight with a plurality of heliostats and reflecting the direct sunlight from the heliostats as reflected sunlight onto a tower receiver, where the reflected sunlight heats a heat transfer fluid in the tower receiver, converting a water stream to a generated steam stream in a steam generator, where the heat transfer fluid provides heat to the steam generator. The generated steam stream is fed to a steam turbine, the steam turbine converts thermal energy in the generated steam stream to mechanical energy to drive an electric generator to generate electricity. The process further includes the steps of heating a fuel feed stream by transferring thermal energy from the heat transfer fluid to create a heated fuel feed stream, such that the heated fuel feed stream reaches a temperature of between 650° C. and 800° C., feeding the heated fuel feed stream to a syngas production cell, where the heated fuel feed stream includes carbon dioxide and water, wherein the carbon dioxide is captured from a flue gas stream, converting the carbon dioxide and water in the heated fuel feed stream to carbon monoxide and hydrogen in the syngas production cell to produce a syngas stream, wherein the syngas production cell includes a solid oxide electrolyte, feeding the syngas stream to a catalytic reactor, wherein the catalytic reactor operates in the presence of a catalyst, and converting the syngas stream to a hydrocarbon fuel stream in the catalytic reactor.

In certain embodiments of the present invention, the syngas production cell includes a solid oxide electrolyzer cell, where the solid oxide electrolyzer cell includes a porous cathode, the solid oxide electrolyte, and a porous anode. In certain embodiments of the present invention, the step of converting the carbon dioxide and water in the heated fuel feed stream to carbon monoxide and hydrogen in the syngas production cell further includes the steps of supplying the electricity to the porous cathode of the solid oxide electrolyzer cell, contacting the porous cathode with fuel feed stream, reducing the carbon dioxide to create carbon monoxide and oxygen ions, wherein the oxygen ions pass through the porous cathode to the solid oxide electrolyte, reducing the water to create hydrogen and oxygen ions, wherein the oxygen ions pass through the porous cathode to the solid oxide electrolyte, diffusing the oxygen ions through the solid oxide electrolyte to the porous anode, and releasing electrons from the oxygen ions at the porous anode, such that oxygen molecules are formed to create an oxygen stream. In certain embodiments of the present invention, the syngas production cell includes a solid oxide fuel wherein the solid oxide fuel cell includes a porous anode, the solid oxide electrolyte, and a porous cathode. In certain embodiments of the present invention, the step of converting the carbon dioxide and water in the heated fuel feed stream to carbon monoxide and hydrogen in the syngas production cell further includes the steps of adding a gaseous hydrocarbon to the heated fuel feed stream, feeding the heated fuel feed stream to the porous anode of the solid oxide fuel cell, reforming the water and the gaseous hydrocarbon in the heated fuel feed stream to create carbon monoxide and hydrogen, reforming the carbon dioxide and the gaseous hydrocarbon in the heated fuel feed stream to create carbon monoxide and hydrogen, reducing oxygen from an oxygen supply on the porous cathode of the solid oxide fuel cell to generate oxygen ions, diffusing the oxygen ions through the solid oxide electrolyte to the porous anode, oxidizing the hydrogen at the porous anode with the oxygen ions to create water and electrons, oxidizing the methane at the porous anode with the oxygen ions to create carbon monoxide, hydrogen, and electrons, and supplying the electrons to an electrical substation, wherein the electrical substation is configured to combine the electrons from the syngas production cell with the electricity generated by the electric generator. In certain embodiments of the present invention, the gaseous hydrocarbon includes methane. In certain embodiments of the present invention, the process further includes the step of feeding the hydrocarbon fuel to a power plant for consumption.

In a second aspect of the present invention, a system to convert carbon dioxide to hydrocarbon fuels using solar energy is provided. The system includes a solar thermal power system configured to convert solar energy to thermal energy and electricity, the solar thermal power system being in thermal communication with a syngas production cell, wherein the syngas production cell is configured to receive thermal energy from the solar thermal power system, the syngas production cell including a fuel side including a fuel inlet configured to receive a fuel feed stream and a fuel outlet configured to receive a syngas stream, and an oxygen side including an oxygen outlet configured to receive an oxygen stream, wherein the fuel feed stream includes carbon dioxide and water, wherein the syngas production cell is configured to convert the carbon dioxide and water into carbon monoxide and hydrogen, the carbon monoxide and hydrogen operable to form the syngas stream, and a catalytic reactor fluidly connected to the fuel side of the syngas production cell, the catalytic reactor being configured to convert the syngas stream from the fuel side of the syngas production cell to a hydrocarbon fuel stream, the catalytic reactor including a reactor bed, the reactor bed including a catalyst and a distributor, wherein the catalytic reactor is configured to operate from 250° C. to 650° C.

In certain embodiments of the present invention, the syngas production cell includes a solid oxide electrolyzer cell. In certain embodiments of the present invention, the solid oxide electrolyzer cell includes a porous cathode in fluid communication with the fuel side of the syngas production cell, the porous cathode having a fuel side of the porous cathode configured to transfer electrons to the fuel feed stream, such that carbon monoxide, hydrogen, and oxygen ions are produced, and an electrolyte side configured to release the oxygen ions into a solid oxide electrolyte, where the porous cathode is configured to allow passage of oxygen ions, a porous anode in fluid communication with the oxygen side of the syngas production cell, the porous anode including an electrolyte side configured to receive oxygen ions from the solid oxide electrolyte, and an outlet side configured to convert oxygen ions to oxygen molecules to form an oxygen stream, where the porous anode is configured to allow passage of oxygen ions, the solid oxide electrolyte, the solid oxide electrolyte lies between the porous cathode and the porous anode, wherein the solid oxide electrolyte is configured to allow passage of oxygen ions, and an electron supply, wherein the electricity from the solar thermal power system provides the electron supply to the porous cathode and accepts electrons from the porous anode. In certain embodiments of the present invention, the porous anode and the porous cathode are selected from the group containing nickel/yttria-stabilized zirconia (Ni-YSZ), Lanthanum Strontium Manganese Oxide-YSZ (LSM-YSZ), and a ceramic oxide of perovskite. In certain embodiments of the present invention, the solid oxide electrolyte contains yttria stabilized zirconia. In certain embodiments of the present invention, the syngas production cell includes a solid oxide fuel cell and the fuel feed stream further includes a gaseous hydrocarbon. In certain embodiments of the present invention, the gaseous hydrocarbon includes methane. In certain embodiments of the present invention, the solid oxide fuel cell includes a porous anode in fluid communication with the fuel side of the syngas production cell, the porous anode comprising a fuel side of the porous anode configured to accept electrons, such that the methane undergoes an oxidation reaction to form carbon monoxide, hydrogen, and electrons, and an electrolyte side configured to accept oxygen ions from a solid oxide electrolyte, where the porous anode is configured to allow passage of oxygen ions, where the methane and water react in the presence of the fuel side of the porous anode to generate carbon monoxide and hydrogen, and where the methane and carbon dioxide react in the presence of the fuel side of the porous anode to generate carbon monoxide and hydrogen, a porous cathode in fluid communication with the oxygen side of the syngas production cell, the porous cathode comprising an outlet side configured to convert oxygen into oxygen ions and an electrolyte side configured to release oxygen ions into the solid oxide electrolyte, where the porous cathode is configured to allow passage of oxygen ions, and the solid oxide electrolyte, the solid oxide electrolyte lies between the porous cathode and the porous anode, wherein the solid oxide electrolyte is configured to allow passage of oxygen ions. In certain embodiments of the present invention, the hydrogen in the fuel side of the syngas production cell undergoes an oxidation reaction to form water and electrons. In certain embodiments of the present invention, the porous cathode and the porous anode are selected from the group containing nickel/yttria-stabilized zirconia (Ni-YSZ), Lanthanum Strontium Manganese Oxide-YSZ (LSM-YSZ), and a ceramic oxide of perovskite. In certain embodiments of the present invention, the solid oxide electrolyte contains yttria stabilized zirconia. In certain embodiments of the present invention, the solar thermal power system includes a tower concentrating solar power system, the tower concentrating solar power system including a tower receiver configured to heat a heat transfer fluid, a plurality of heliostats in proximity to the tower receiver, wherein the heliostats are configured to receive direct sunlight and reflect the direct sunlight from the heliostats as reflected sunlight onto the tower receiver, a hot storage tank fluidly connected to the tower receiver, the hot storage tank configured to store the heat transfer fluid, a steam generator fluidly connected to the hot storage tank, the steam generator configured to transfer heat from the heat transfer fluid to a water stream to create a generated steam stream, a steam turbine fluidly connected to the steam generator, wherein the generated steam stream is configured to drive the steam turbine, and an electric generator mechanically connected to the steam turbine, where the steam generator is configured to drive the electric generator to create electricity. In certain embodiments of the present invention, the syngas production cell operates from 650° C. to 800° C. In certain embodiments of the present invention, the system to convert carbon dioxide to hydrocarbon fuels further includes a carbon capture system configured to remove carbon dioxide from a flue gas stream to create a carbon dioxide stream, the carbon capture system in fluid communication with a power plant, wherein the power plant is configured to produce a flue gas stream.

BRIEF DESCRIPTION OF THE DRAWINGS

These and other features, aspects, and advantages of the present invention will become better understood with regard to the following descriptions, claims, and accompanying drawings. It is to be noted, however, that the drawings illustrate only several embodiments of the invention and are therefore not to be considered limiting of the invention's scope as it can admit to other equally effective embodiments.

DETAILED DESCRIPTION OF THE INVENTION

While the invention will be described with several embodiments, it is understood that one of ordinary skill in the relevant art will appreciate that many examples, variations and alterations to the apparatus and methods described herein are within the scope and spirit of the invention. Accordingly, the exemplary embodiments of the invention described herein are set forth without any loss of generality, and without imposing limitations, on the claimed invention.

Figure 1:
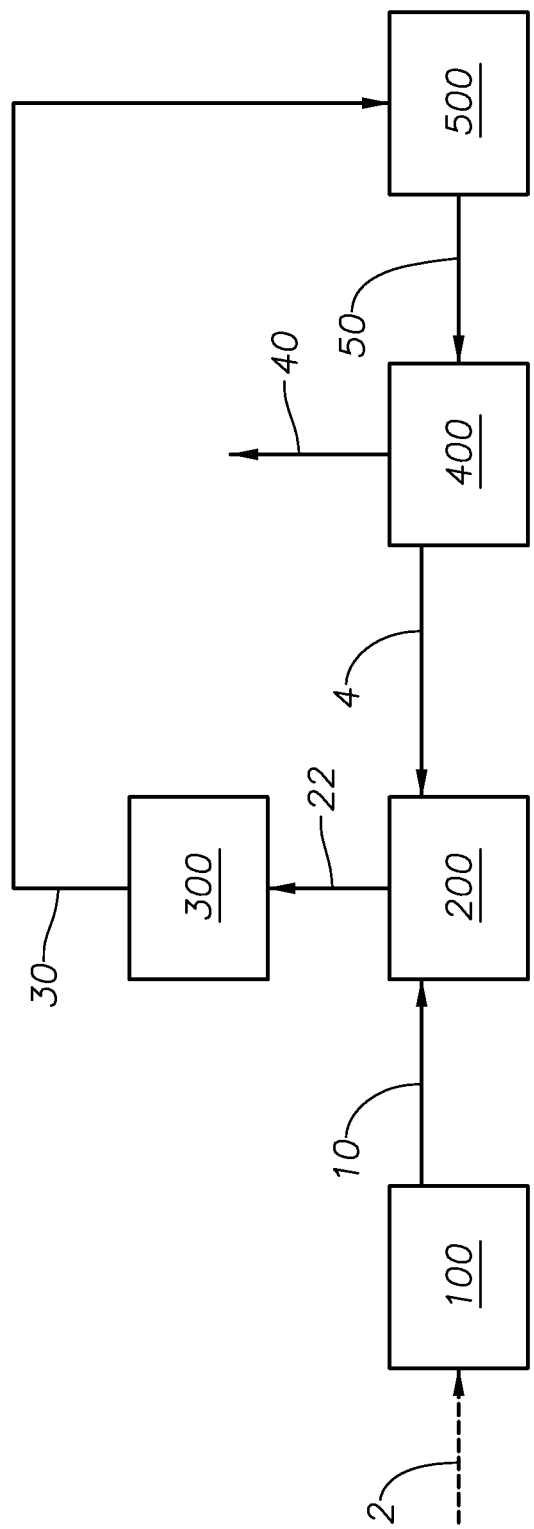
FIG. 1 is a process flow diagram of an embodiment of the present invention.

FIG. 1 provides a process flow diagram of an embodiment of the present invention. Solar thermal power system 100 converts direct sunlight 2 into thermal energy 10. Direct sunlight 2 consists of solar energy across all wavelengths. Solar thermal power system 100 can be any type of solar thermal power system that can convert solar energy to thermal energy and electricity.

Carbon capture system 400 separates $CO_2$ from flue gas 50 of operating unit 500 and generates waste gas 40. Waste gas stream 40 is disposed of as required by the composition of the stream. In at least one embodiment of the present invention, waste gas stream 40 is vented to atmosphere.

The $CO_2$ from carbon capture system 400 is mixed with other streams (not shown) to create fuel feed stream 4. Fuel feed stream 4 contains $CO_2$. In at least one embodiment of the present invention, fuel feed stream 4 contains $H_2O$, in addition to $CO_2$. In at least one embodiment of the present invention, fuel feed stream contains $CO_2$, $H_2O$, and gaseous hydrocarbons. Exemplary gaseous hydrocarbons include methane ($CH_4$), ethane ($C_2H_6$), butane ($C_3H_8$), and combinations thereof. In at least one embodiment of the present invention, fuel feed stream 4 contains $CO_2$, $H_2O$, and $CH_4$. In at least one embodiment of the present invention, fuel feed stream 4 contains $CO_2$, $H_2O$, and $CH_4$, and inert gases. In at least one embodiment, fuel feed stream 4 is in the absence of nitrogen containing compounds and sulfur containing compounds. The exact temperature, pressure, and composition of fuel feed stream 4 will depend on the streams that are mixed together to create fuel feed stream 4.

Operating unit 500 can be any type of operating unit that produces an exhaust gas, a flue gas, or waste gas containing $CO_2$. Operating unit 500 includes, for example, a power plant that burns fossil fuels or other hydrocarbons and produces electricity, a steel mill which produces $CO_2$ as a waste gas of the process, or any other type of production unit. Flue gas 50 includes, for example, any type of flue gas that contains an amount of $CO_2$. In accordance with at least one embodiment of the present invention, flue gas 50 includes an amount of $CO_2$ and an amount of $H_2O$. In accordance with at least one embodiment, operating unit 500 is a power plant. In at least one embodiment of the present invention, flue gas 50 is from a gas-fired power plant and has a composition of between about 7.4% and about 7.7% $CO_2$, about 14.6% about 4.45% $O_2$, and between about 73% and about 74% $N_2$, with the remainder including nitrogen containing compounds, sulfur containing compounds, and various other gases. Alternately, flue gas 50 from, for example, a coal-fired power plant can have a composition of between about 12.5% and about 12.8% $CO_2$, about 6.2% $H_2O$, about 4.4% $O_2$, and between about 76% and about 77% $N_2$, with the remainder including nitrogen containing compounds, sulfur containing compounds, and various other gases.

In accordance with one embodiment, flue gas 50 is subjected to scrubbing technologies (not shown) prior to feeding to carbon capture system 400. Any known scrubbing technologies capable of removing sulfur and nitrogen containing compounds from flue gas 50 can be used. Scrubbing technologies can optionally remove particulate matters. Conventional scrubbing technologies include wet scrubbers and electrostatic separators.

Thermal energy 10 provides heat to syngas production cell 200, heating syngas production cell 200 to a temperature between about 500° C. and about 1000° C., alternately between about 600° C. and about 900° C., alternately between about 650° C. and about 800° C., and alternately between about 700° C. and about 800° C. Heat from thermal energy 10 can be transferred by a heat exchanger (not shown) to heat the feed streams to syngas production cell 200. In at least one embodiment of the present invention, thermal energy 10 provides heat to fuel feed stream 4 to create the heated fuel feed stream (not shown) to syngas production cell 200.

Syngas production cell 200 uses thermal energy 10 to convert fuel feed stream 4 to syngas stream 22. Syngas stream 22 contains synthesis gas, or syngas. Syngas is a gas stream containing a combination of CO and $H_2$. In at least one embodiment of the present invention, syngas stream 22 also contains $CO_2$ and $H_2O$. The exact composition of syngas stream 22 is determined after consideration of the temperature, pressure, and configuration of syngas production cell 200.

Syngas stream 22 is fed to catalytic reactor 300. Catalytic reactor 300 converts the syngas in syngas stream 22 to hydrocarbons to create hydrocarbon fuel stream 30. In at least one embodiment, hydrocarbon fuel stream 30 include alkanes, alcohols, acids, ethers, and combinations thereof. The composition of hydrocarbon fuel stream 30 depends on the catalyst used in catalytic reactor 300 and the composition of syngas stream 22. In at least one embodiment of the present invention, any catalyst which converts CO and $H_2$ to hydrocarbons is used in catalytic reactor 300. Exemplary catalysts include a Fischer-Tropsch catalyst, a methanation catalyst, or combinations thereof. The catalyst can include transition metals such as iron, cobalt, nickel, copper, zinc, ruthenium, rhodium, palladium, platinum, or combinations thereof. Catalytic reactor 300 operates a temperature of between about 200° C. and about 700° C., alternately between about 250° C. and about 650° C., and alternately between about 300° C. and about 600° C. In accordance with at least one embodiment of the present invention, at operating conditions of 300° C. and high pressures the catalyst is a blend of copper and zinc oxide. In other embodiments of the present invention, at operating conditions of 600° C. and low pressures, the catalyst includes iron. Catalysts can include a catalyst support, such as a zeolite. The distributor (not shown) supports the catalyst in catalytic reactor 300, the size and shape of the distributor is dependent on the type of catalytic reactor 300 and the type of catalyst. Catalysts are chosen in consideration of the operating conditions in catalytic reactor 300 and the reaction product composition desired. According to various embodiments, catalytic reactor 300 includes a packed bed reactor or a fluidized bed reactor.

According to one embodiment of the present invention, the catalyst is chosen such that the catalytic conversion of syngas stream 22 to hydrocarbon fuel stream 30 occurs according to the following reaction:

$$(2n+1)H_2 + nCO \rightarrow C_nH_{(2n+2)} + nH_2O$$

In at least one embodiment of the present invention, conversion of syngas stream 22 creates $CH_4$ and $H_2O$ (n=1).

In an alternate embodiment of the present invention, the catalyst is chosen such that the catalytic conversion of syngas stream 22 to hydrocarbon fuel stream 30 includes the following reactions:

$$2H_2 + CO \rightarrow CH_3OH$$

$$2CH_3OH \rightarrow CH_3OCH_3 + H_2O$$

$$CO + CH_3OH \rightarrow CHO_2CH_3$$

$$CHO_2CH_3 + H_2O \rightarrow CHO_2H + CH_3OH$$

The reaction products of the above reactions include methanol ($CH_3OH$), dimethyl ether (DME) ($CH_3OCH_3$), and formic acid ($CHO_2H$).

Hydrocarbon fuel stream 30 is fed to operating unit 500. In certain embodiments, hydrocarbon fuel stream 30 can be stored (not shown) or transported offsite (not shown). In at least one embodiment, hydrocarbon fuel stream 30 undergoes additional processing steps to separate the components of hydrocarbon fuel stream 30. In at least one embodiment of the present invention, the additional processing steps separate $H_2O$ from hydrocarbon fuel stream 30.

Notably, the embodiment of the invention as shown and described in FIG. 1 creates a hydrocarbon fuel useful for power generation, without the use of a fossil fuel at any stage in the system.

Figure 2:
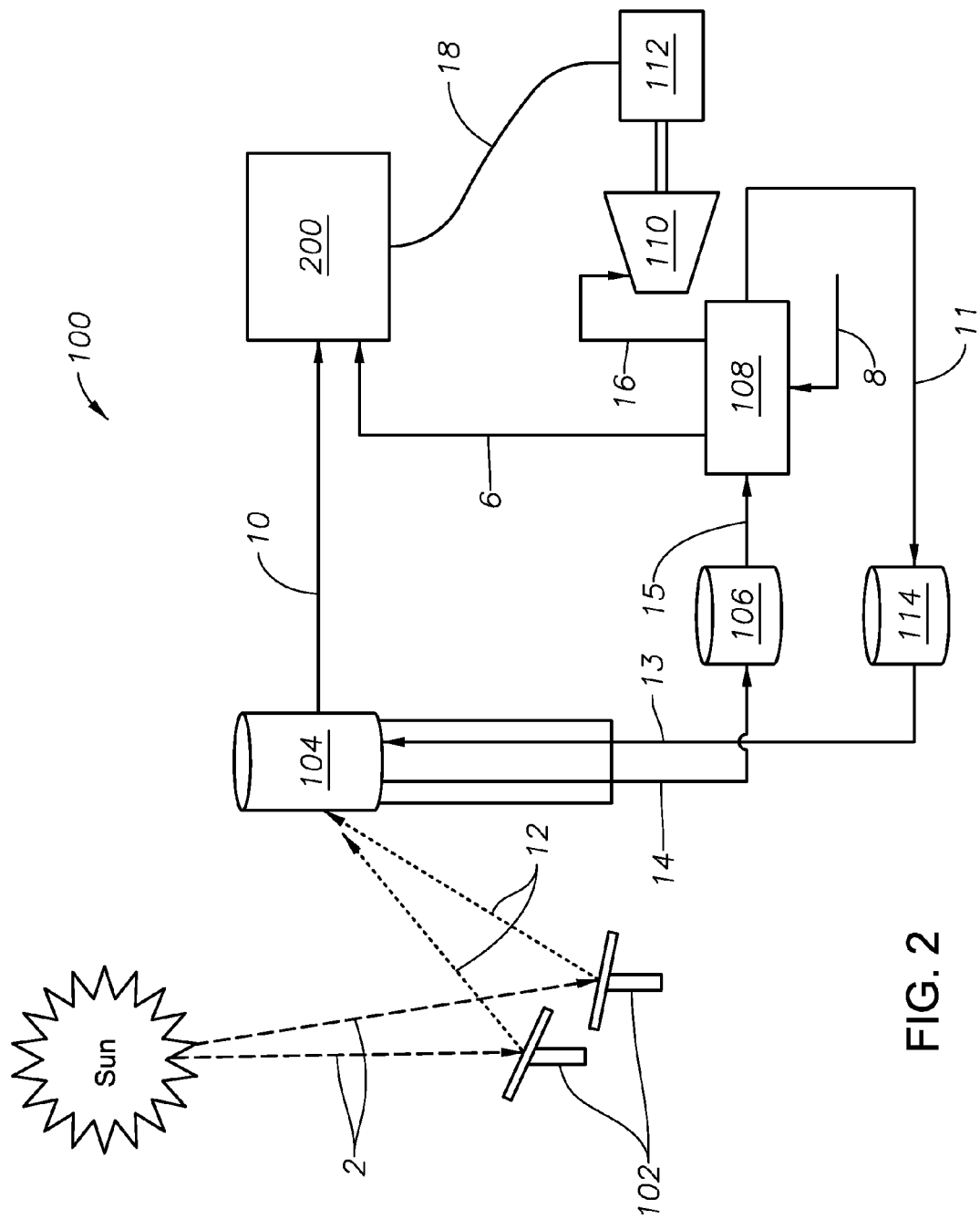
FIG. 2 is a schematic of an embodiment of the solar thermal power system.

FIG. 2 provides a schematic of an embodiment of solar thermal power system 100. According to this embodiment, direct sunlight 2 hits heliostats 102 and reflected sunlight 12 is focused onto tower receiver 104. Heliostats 102 are designed to reflect specific wavelengths of direct sunlight 2, such that direct sunlight 2 can be converted to thermal energy, electricity, or mechanical energy. Reflected sunlight 12 is solar energy across the specific wavelengths reflected by heliostats 102. Tower receiver 104 provides thermal energy 10 from the sunlight to syngas production cell 200, as described in reference to FIG. 1.

According to various embodiments, tower receiver 104 focuses reflected sunlight 12 to raise the temperature of heat transfer fluid 14. Heat transfer fluid 14 includes, for example, any heat transfer fluid, including water, salt water, or a molten salt, such as sodium nitrate salt, potassium nitrate salt, calcium nitrate salt, lithium nitrate salt, or combinations thereof. Other molten salts include, for example, lithium, sodium, potassium, rubidium, cesium, francium, beryllium, magnesium, calcium, strontium, barium, radium, fluorine, chlorine, bromine, and iodine. Molten salts have an advantage over water because they retain heat for longer periods of time. In at least one embodiment of the present invention, heat transfer fluid 14 includes a blend of sodium chloride and potassium chloride, Heat transfer fluid 14 reaches a temperature between about 500° C. and about 1000° C., alternately between about 600° C. and about 900° C., alternately between about 650° C. and about 800° C., and alternately between about 700° C. and about 800° C.

According to various embodiments, heat transfer fluid 14 can be stored in hot storage tank 106 for later use (i.e., when there is no longer direct sunlight 2) as stored transfer fluid 15. When needed, stored transfer fluid 15 is fed from hot storage tank 106 to steam generator 108. Steam generator 108 transfers heat from stored transfer fluid 15 to water stream 8 to create generated steam stream 16 and steam supply 6. Steam generator 108 can be any device capable of producing steam to operate a turbine. Steam generator 108 includes, for example, a boiler or a supercritical steam generator (Benson boiler). Water stream 8 originates from any source of water capable of producing steam. According to various embodiments, steam supply 6 is fed in syngas production cell 200. Steam supply 6 provides both $H_2O$ (as vapor) and heat to syngas production cell 200.

Steam generator 108 extracts heat from stored transfer fluid 15 and creates used transfer fluid 11. According to at least one embodiment used transfer fluid 11 is stored in cold storage tank 114 as cold transfer fluid 13. When needed, cold transfer fluid 13 is fed from cold storage tank 114 to tower receiver 104, where it is heated and becomes heat transfer fluid 14.

As used herein, heat transfer fluid 14, stored transfer fluid 15, used transfer fluid 11, and cold transfer fluid 13 are the same fluid at different stages in the solar thermal process.

According to various embodiments, generated steam stream 116 is fed to steam turbine 110, steam turbine 110 converts the thermal energy in generated steam stream 16 to mechanical energy (i.e., a rotating shaft), the mechanical energy drives electric generator 112. Steam turbine 110 includes, for example, any type of steam turbine including condensing, non-condensing, reheat, extraction, and induction. The rating/size of the turbine will depend on the quantity of electricity produced by electric generator 112. Electric generator 112 generates electricity 18. Examples of electric generators useful in this invention include Seebeck generators and thermoelectric generators. Electricity 18 provides electricity to syngas production cell 200. In at least one embodiment of the present invention, electricity 18 provides electricity to other process units (not shown), to an electrical substation (not shown), or to the local electric grid (not shown). In at least one embodiment of the present invention, solar thermal power system 100 is capable of generating up to about 200 MW of electricity.

Figure 3:
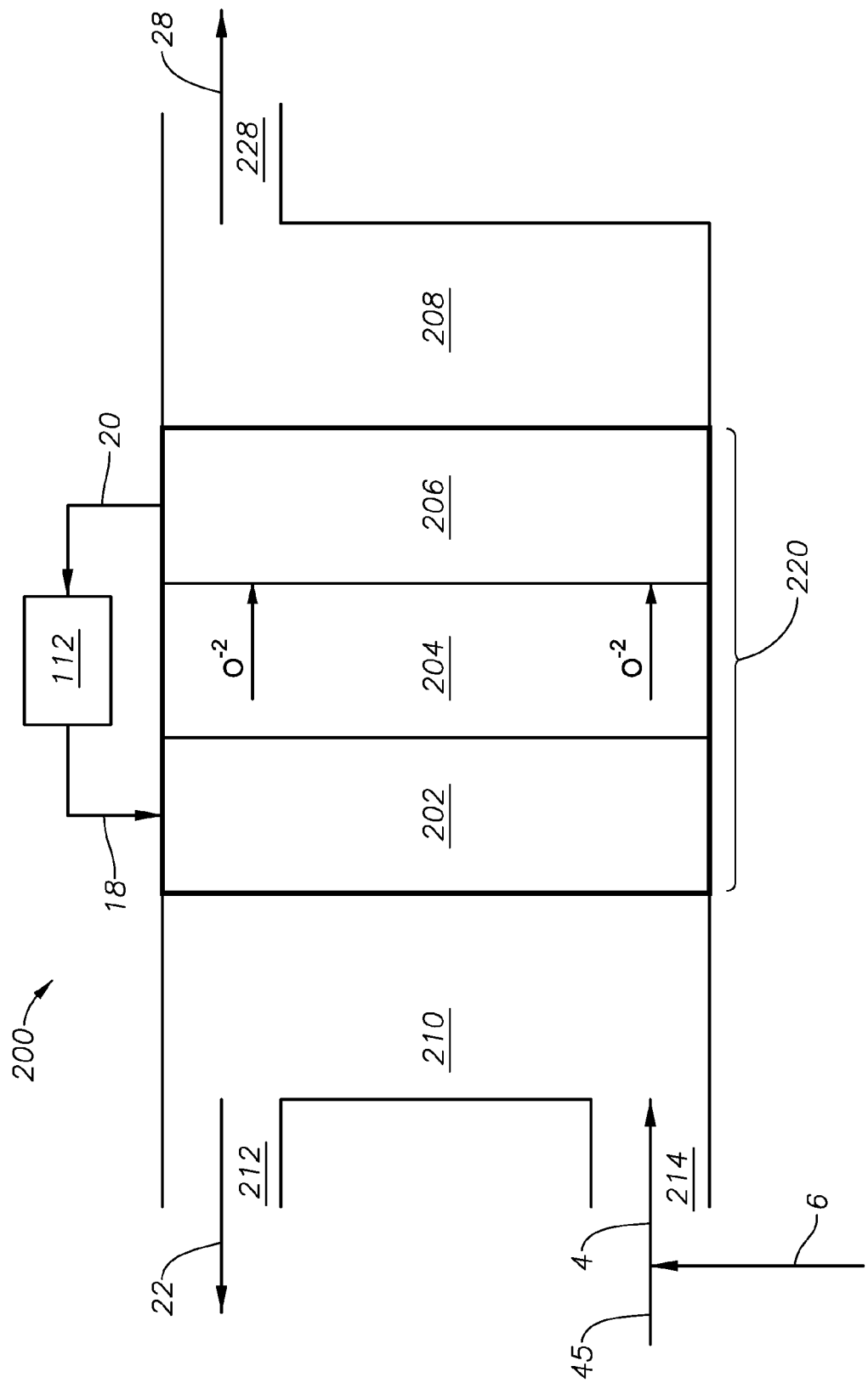
FIG. 3 is a plan view of an embodiment of the syngas production cell.

FIG. 3 provides a plan view of an embodiment of syngas production cell 200, wherein syngas production cell 200 includes solid oxide electrolyzer cell (SOEC) 220. SOEC 220 includes porous cathode 202, solid oxide electrolyte 204, and porous anode 206. Electricity 18 provides electrons to porous cathode 202, thus porous cathode 202 is negatively charged. Porous cathode 202 can be any material that allows for the transfer of electrons and/or negatively charged ions through the material. In at least one embodiment of the present invention, porous cathode 202 is any material that allows the electrons to pass through to react with components in fuel side 210. In at least one embodiment, the material of porous cathode 202 allows the transfer of electrons from porous cathode 206 to $CO_2$ and $H_2O$ in fuel side 210 and allows oxygen ions to diffuse through from fuel side 210 to the electrolyte side (not shown). Porous cathode 202 can be a cermet, a composite material of ceramic and a metal. Cermets include, for example, nickel/yttria-stabilized zirconia (Ni-YSZ) or Lanthanum Strontium Manganese Oxide-YSZ (LSM-YSZ). In accordance with one embodiment of the present invention, porous cathode 202 is a ceramic oxide of perovskite. In at least one embodiment of the present invention, porous cathode 202 does not include a liquid or an aqueous solution.

As shown in FIG. 3, carbon dioxide stream 45 mixes with steam supply 6 to create fuel feed stream 4. Carbon dioxide stream 45 contains $CO_2$. In at least one embodiment of the present invention, carbon dioxide stream 45 also contains $H_2O$. Fuel feed stream 4 enters syngas production cell 200 on fuel side 210 at fuel inlet 214. In an alternate embodiment of the present invention, fuel feed stream 4 and steam supply 6 enters syngas production cell 200 through separate inlets. In at least one embodiment of the present invention, prior to entering fuel inlet 214, fuel feed stream 4 is heated by transfer of heat from thermal energy 10 (not shown) to create the heated fuel feed stream (not shown) at a temperature of between 500° C. and about 1000° C., alternately between about 600° C. and about 900° C., alternately between about 650° C. and about 800° C., and alternately between about 700° C. and about 800° C. Thermal energy 10 helps drive the electrochemical reaction.

In at least one embodiment of the present invention, the streams on fuel side 210 of syngas production cell 200 are in a gas phase, occurring in the absence of a liquid or aqueous phase.

Fuel feed stream 4 contacts the fuel side of porous cathode 202 of SOEC 220. On contact, porous cathode 202 provides electrons to the $CO_2$ and the $H_2O$ in fuel feed stream 4, which results in the co-electrolysis (reduction reactions) of $CO_2$ and $H_2O$.

The reduction reactions of $CO_2$ and $H_2O$ proceed according to the following chemistry:

$$2H_2O + 4e^- \rightarrow 2H_2 + 2O^{2-} \quad \text{(reaction 1)}$$

$$2CO_2 + 4e^- \rightarrow 2CO + 2O^{2-} \quad \text{(reaction 2)}$$

In reaction 1, hydrogen molecules and oxygen ions are produced at porous cathode 202. In reaction 2, carbon monoxide molecules and oxygen ions are produced at porous cathode 202. The co-electrolysis of fuel feed stream 4 creates syngas stream 22, as described in reference to FIG. 1.

According to at least one embodiment, the oxygen ions created in the reduction reactions of $CO_2$ and $H_2O$ move through porous cathode 202 to solid oxide electrolyte 204. The oxygen ions then pass through solid oxide electrolyte 204 to porous anode 206. In accordance with at least one embodiment of the present invention, solid oxide electrolyte 204 includes yttria stabilized zirconia. In accordance with another embodiment of the present invention, solid oxide electrolyte 204 includes cerium(IV) oxide ($CeO_2$) mixed with zirconia. In at least one embodiment of the present invention solid oxide electrolyte 204 is in the absence of a liquid or an aqueous phase.

Electron return 20 allows electrons to flow from porous anode 206, thus porous anode 206 is positively charged. The oxygen ions pass through solid oxide electrolyte 204 and then pass through porous anode 206. The oxygen ions release electrons on oxygen side (not shown) of porous anode 206 on oxygen side 208 of syngas production cell 200. In at least one embodiment of the present invention, oxygen side 208 of syngas production cell 200 is in the absence of $H_2$ or $H_2$ evolution. The oxygen ions on oxygen side of porous anode 206 undergo an oxidation reaction to form oxygen molecules, according to the following reaction:

$$2O^{2-} \rightarrow O_2 + 4e^-$$

Porous anode 206 includes, for example, any material which allows oxygen ions to pass through from the electrolyte side (not shown) and accepts electrons from oxygen ions to form oxygen molecules on the oxygen side (not shown). Porous anode 206 includes, for example, a cermet, a composite material of ceramic and a metal. Cermets include, for example, nickel/yttria-stabilized zirconia (Ni-YSZ) or Lanthanum Strontium Manganese Oxide-YSZ (LSM-YSZ). In accordance with one embodiment of the present invention, porous anode 206 includes a ceramic oxide of perovskite. In at least one embodiment of the present invention porous anode 206 is in the absence of a liquid or an aqueous phase.

The oxygen molecules, as oxygen stream 28, exit oxygen side 208 of syngas production cell 200 through oxygen outlet 228. In at least one embodiment of the present invention, oxygen side 208 is in the absence of a liquid or an aqueous phase. In accordance with at least one embodiment, oxygen stream 28 is stored, fed to another processing unit, or transported to another location.

In at least one embodiment of the present invention, syngas production cell 200, with SOEC 220 is a net consumer of electricity.

Figure 4:
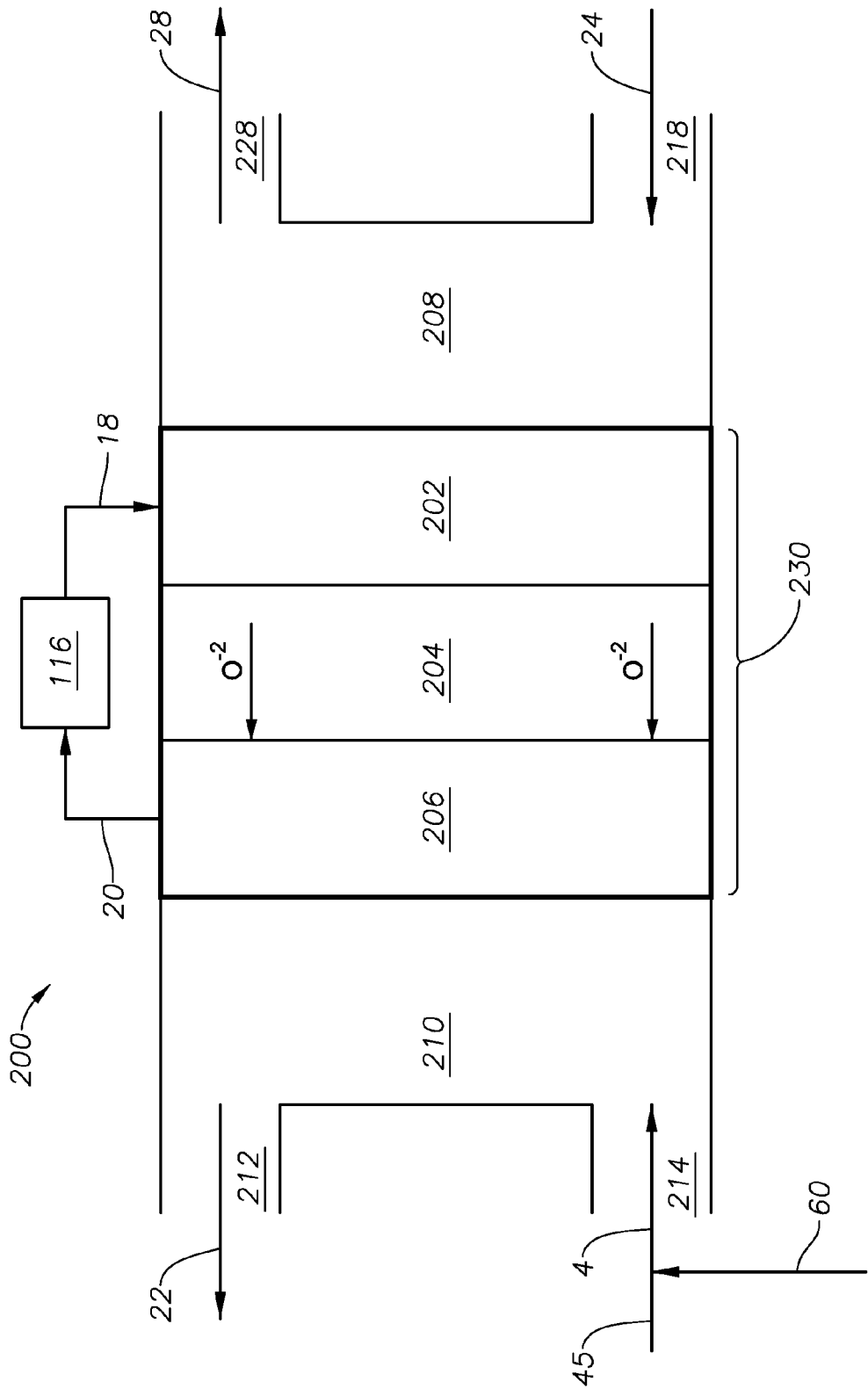
FIG. 4 is a plan view of an embodiment of the syngas production cell.

FIG. 4 provides a plan view of an embodiment of syngas production cell 200, where syngas production cell 200 includes solid oxide fuel (SOFC) 230. SOFC 230 includes porous anode 206, solid oxide electrolyte 204, and porous cathode 202, as described with reference to FIG. 3.

According to one embodiment of syngas production cell 200 as shown in FIG. 4, fuel feed stream 4 is a mix of carbon dioxide stream 45 and methane stream 60. Methane stream 60 can be any source of a gaseous hydrocarbon. In at least one embodiment of the present invention, methane stream 60 contains gaseous hydrocarbons. In at least one embodiment of the present invention, methane stream 60 includes any hydrocarbons that are gaseous at the operating temperature of syngas production cell 200. In at least one embodiment of the present invention, methane stream 60 contains hydrocarbons that are gaseous at standard temperature and pressure. In at least one embodiment of the present invention, methane stream 60 includes $CH_4$, $C_2H_6$, $C_3H_8$, and combinations thereof. In at least one embodiment of the present invention, methane stream 60 includes $CH_4$.

In at least one embodiment of the present invention, fuel feed stream 4 includes $CO_2$, $H_2O$, and $CH_4$. Fuel feed stream 4 enters syngas production cell 200 on fuel side 210 at fuel inlet 214. In an alternate embodiment of the present invention, fuel feed stream 4 and methane stream 60 enter syngas production cell 200 through separate inlets. In at least one embodiment of the present invention, steam is also fed to fuel side 210 of syngas production cell 200 at anode 206. In at least one embodiment of the present invention, fuel feed stream 4 is in the gas phase, occurring in the absence of a liquid or aqueous phase.

At anode 206 the components, $CO_2$, $CH_4$, and $H_2O$ of fuel feed stream 4 undergo reforming reactions (steam reforming and dry reforming) and oxidation reactions to produce the syngas in syngas stream 22. In at least one embodiment of the present invention, anode 206 acts as a catalyst for the reforming reactions. The reforming reactions proceed according to the following chemistry:

$$H_2O + CH_4 \rightarrow CO + 3H_2$$

$$CO_2 + CH_4 \rightarrow 2CO + 2H_2$$

The oxidation reactions proceed according to the following chemistry:

$$H_2 + O^{2-} \rightarrow H_2O + 2e^-$$

$$CH_4 + O^{2-} \rightarrow CO + 2H_2 + 2e^-$$

The oxygen ions of the oxidation reactions are produced at porous cathode 202 on oxygen side 208. Oxygen supply 24 is fed to oxygen side 208 through oxygen inlet 218. Oxygen supply 24 can be any source of oxygen. In at least one embodiment of the present invention, oxygen supply 24 is a pure source of oxygen ($O_2$). In an alternate embodiment of the present invention, oxygen supply 24 is air. In at least one embodiment of the present invention, oxygen supply 24 is oxygen-enriched air.

Electricity 18 supplies electrons to porous cathode 202, so porous cathode 202 is negatively charged. The $O_2$ in oxygen supply 24 contacts porous cathode 202 and oxygen ions ($O^{2-}$) are generated. Excess oxygen supply 24 exits syngas production cell 200 through oxygen stream 28.

The oxygen ions diffuse through porous cathode 202 to solid oxide electrolyte 204. The oxygen ions diffuse through solid oxide electrolyte 204 to porous anode 206. The oxygen ions diffuse through porous anode 206 to fuel side 210, where they react according to the oxidation reactions above.

The electrons released in the oxidation reactions pass through porous anode 206 and are carried by electron return 20 to electrical substation 116. Electrical substation 116 combines electricity produced by solar thermal power system 100 (not shown) with electricity in electron return 20 generated from syngas production cell 200. Electrical substation 116 can be used to supply the local electric grid (not shown) or can be used at other processing units (not shown).

In at least one embodiment of the present invention, syngas production cell 200 with SOFC 230 is a net producer of electricity.

Figure 5:
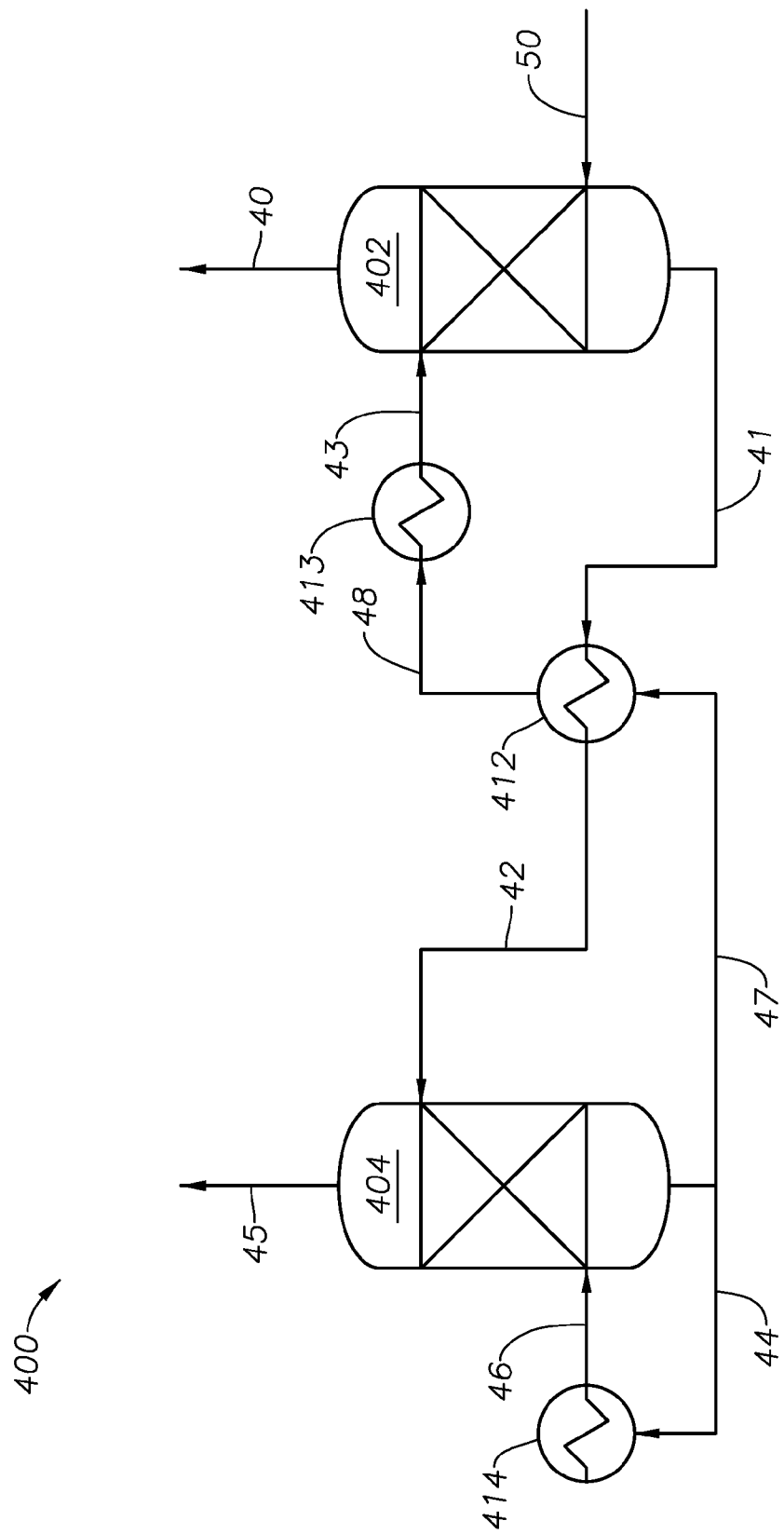
FIG. 5 is a schematic of an embodiment of the carbon capture system.

FIG. 5 is a schematic of an embodiment of carbon capture system 400. Carbon capture system 400 can be any carbon capture system capable of isolating $CO_2$ and/or $H_2O$ from flue gas stream 50. Carbon capture system 400 includes, for example, any type of post-combustion, pre-combustion, or oxyfuel system. One conventional carbon capture system is described as an example. One of skill in the art will appreciate that any carbon capture system must be adjusted to account for the composition of the flue gas and the desired composition of the fuel feed stream.

In accordance with one embodiment, flue gas 50 is fed from operating unit 500 (not shown) as described with reference to FIG. 1. Flue gas 50 is fed to the bottom of absorber 402 and flows up to the top of absorber 402. Absorber 402 contains solvent from solvent stream 43 (i.e., a lean solvent stream, as discussed below) fed to the top of absorber 402. The solvent in absorber 402 includes, for example, an amine solvent, such as potassium carbonate, or an organic amine. Absorber 402 includes, for example, any type of absorption unit including a membrane absorber, a packed bed absorber, or a frayed column absorber. As solvent stream 43 flows down through the absorber, the solvent in solvent stream 43 contacts flue gas 50 flowing up through absorber 402. The $CO_2$ and at least some of the H₂O vapor in flue gas 50 are absorbed into the solvent creating carbon dioxide rich solvent 41 which exits at the bottom of absorber 402. In accordance with one embodiment of the present invention, carbon dioxide rich solvent 41 is in the absence of H₂O vapor. In accordance with at least one embodiment of the present invention, carbon dioxide rich solvent 41 includes all or substantially all of the H₂O vapor in flue gas 50. Waste gas 40, containing essentially no $CO_2$, exits the top of absorber 402 and can undergo further processing and disposal steps as necessary for local environmental regulations, including, for example, scrubbing technologies and flare technologies.

As shown in FIG. 5, carbon dioxide rich solvent 41 is fed to heat exchanger 412. Heat exchanger 412 is, for example, a cross exchanger, where the heat from carbon dioxide lean solvent 47 is used to heat carbon dioxide rich solvent 41.

Warmed carbon dioxide rich solvent 42 is fed to the top of regenerator 404. Regenerator 404 can be any type of unit (e.g., a stripping unit) capable of handling the desorption of $CO_2$ from a solvent. Regenerator 404 includes, for example, reboiler 414 which heats bottoms carbon dioxide solvent 44 to a temperature between about 80° C. to about 120° C. The exact operating conditions depend on the type of solvent and the composition of $CO_2$ desired. Hot carbon dioxide solvent 46 enters regenerator 404 where the $CO_2$ separates from the solvent and exits as carbon dioxide stream 45.

Carbon dioxide lean solvent 47 is fed to heat exchanger 412 where some of the heat from carbon dioxide lean solvent 47 is removed. Lean solvent 48 is then fed to chiller 413 where the stream is cooled to below about 40° C. Solvent stream 43 is then fed back to absorber 402.

Carbon dioxide stream 45 can be fed directly to syngas production cell 200 or can be mixed with other stream to create fuel feed stream 4 as described with reference to FIGS. 1, 3, and 4.

Although the present invention has been described in detail, it should be understood that various changes, substitutions, and alterations can be made hereupon without departing from the principle and scope of the invention. Accordingly, the scope of the present invention should be determined by the following claims and their appropriate legal equivalents.

The singular forms "a," "an," and "the" include plural referents, unless the context clearly dictates otherwise.

Optional or optionally means that the subsequently described event or circumstances can or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

Throughout this application, where patents or publications are referenced, the disclosures of these references in their entireties are intended to be incorporated by reference into this application, in order to more fully describe the state of the art to which the invention pertains, except when these references contradict the statements made herein.

As used herein and in the appended claims, the words "comprise," "has," and "include" and all grammatical variations thereof are each intended to have an open, non-limiting meaning that does not exclude additional elements or steps.

As used herein, terms such as "first" and "second" are arbitrarily assigned and are merely intended to differentiate between two or more components of an apparatus. It is to be understood that the words "first" and "second" serve no other purpose and are not part of the name or description of the component, nor do they necessarily define a relative location or position of the component. Furthermore, it is to be understood that that the mere use of the term "first" and "second" does not require that there be any "third" component, although that possibility is contemplated under the scope of the present invention.

What is claimed is:

1. A process for converting carbon dioxide to hydrocarbon fuels using solar energy, the process comprising the steps of:
   receiving direct sunlight with a plurality of heliostats and reflecting the direct sunlight from the heliostats as reflected sunlight onto a tower receiver, wherein the reflected sunlight heats a heat transfer fluid in the tower receiver;
   converting a water stream to a generated steam stream in a steam generator, wherein the heat transfer fluid provides heat to the steam generator;
   feeding the generated steam stream to a steam turbine, wherein the steam turbine converts thermal energy in the generated steam stream to mechanical energy to drive an electric generator to generate electricity;
   heating a fuel feed stream by transferring thermal energy from the heat transfer fluid to create a heated fuel feed stream, such that the heated fuel feed stream reaches a temperature of between 650° C. and 800° C.;
   feeding the heated fuel feed stream to a syngas production cell, wherein the heated fuel feed stream comprises carbon dioxide and water, wherein the carbon dioxide is captured from a fuel gas stream, wherein the syngas production cell comprises a solid oxide electrolyzer cell, wherein the solid oxide electrolyzer cell comprises a porous cathode, the solid oxide electrolyte, and a porous anode;
   converting the carbon dioxide and water in the heated fuel feed stream to carbon monoxide and hydrogen in the syngas production cell to produce a syngas stream, wherein the syngas production cell comprises a solid oxide electrolyte;
   feeding the syngas stream to a catalytic reactor, wherein the catalytic reactor operates in the presence of a catalyst; and
   converting the syngas stream to a hydrocarbon fuel stream in the catalytic reactor.

2. The process as claimed in claim 1, wherein the step of converting the carbon dioxide and water in the heated fuel feed stream to carbon monoxide and hydrogen in the syngas production cell further comprises the steps of:
   supplying the electricity to the porous cathode of the solid oxide electrolyzer cell;
   contacting the porous cathode with the heated fuel feed stream;
   reducing the carbon dioxide to create carbon monoxide and oxygen ions, wherein the oxygen ions pass through the porous cathode to the solid oxide electrolyte;
   reducing the water to create hydrogen and oxygen ions, wherein the oxygen ions pass through the porous cathode to the solid oxide electrolyte;
   diffusing the oxygen ions through the solid oxide electrolyte to the porous anode; and
   releasing electrons from the oxygen ions at the porous anode, such that oxygen molecules are formed to create an oxygen stream.

3. The process as claimed in claim 1, further comprising the step of:

feeding the hydrocarbon fuel to a power plant for consumption.

4. A process for converting carbon dioxide to hydrocarbon fuels using solar energy, the process comprising the steps of:

receiving direct sunlight with a plurality of heliostats and reflecting the direct sunlight from the heliostats as reflected sunlight onto a tower receiver, wherein the reflected sunlight heats a heat transfer fluid in the tower receiver;

converting a water stream to a generated steam stream in a steam generator, wherein the heat transfer fluid provides heat to the steam generator;

feeding the generated steam stream to a steam turbine, wherein the steam turbine converts thermal energy in the generated steam stream to mechanical energy to drive an electric generator to generate electricity;

heating a fuel feed stream by transferring thermal energy from the heat transfer fluid to create a heated fuel feed stream, such that the heated fuel feed stream reaches a temperature of between 650° C. and 800° C.;

feeding the heated fuel feed stream to a syngas production cell, wherein the heated fuel feed stream comprises carbon dioxide and water, wherein the carbon dioxide is captured from a fuel gas stream, wherein the syngas production cell comprises a solid oxide electrolyzer cell, wherein the solid oxide fuel cell comprises a porous anode, the solid oxide electrolyte, and a porous cathode;

converting the carbon dioxide and water in the heated fuel feed stream to carbon monoxide and hydrogen in the syngas production cell to produce a syngas stream, wherein the syngas production cell comprises a solid oxide electrolyte;

feeding the syngas stream to a catalytic reactor, wherein the catalytic reactor operates in the presence of a catalyst; and converting the syngas stream to a hydrocarbon fuel stream in the catalytic reactor.

5. The process as claimed in claim 4, wherein the step of converting the carbon dioxide and water in the heated fuel feed stream to carbon monoxide and hydrogen in the syngas production cell further comprises the steps of:

adding a gaseous hydrocarbon to the heated fuel feed stream;

feeding the heated fuel feed stream to the porous anode of the solid oxide fuel cell;

reforming the water and the gaseous hydrocarbon in the heated fuel feed stream to create carbon monoxide and hydrogen;

reforming the carbon dioxide and the gaseous hydrocarbon in the heated fuel feed stream to create carbon monoxide and hydrogen;

reducing oxygen from an oxygen supply on the porous cathode of the solid oxide fuel cell to generate oxygen ions;

diffusing the oxygen ions through the solid oxide electrolyte to the porous anode;

oxidizing the hydrogen at the porous anode with the oxygen ions to create water and electrons;

oxidizing the methane at the porous anode with the oxygen ions to create carbon monoxide, hydrogen, and electrons; and supplying the electrons to an electrical substation, wherein the electrical substation is configured to combine the electrons from the syngas production cell with the electricity generated by the electric generator.

6. The process as claimed in claim 5, wherein the gaseous hydrocarbon comprises methane.

* * * * *